(12) United States Patent
Von Wendorff et al.

(10) Patent No.: US 10,802,597 B2
(45) Date of Patent: Oct. 13, 2020

(54) ASSIGNING A TOOL TO A PICK-UP GESTURE

(71) Applicant: Siemens Healthcare GmbH, Erlangen (DE)

(72) Inventors: Cynthia Von Wendorff, Spardorf (DE); Barbara Laermann, Munich (DE); Nitin Bagrecha, Nuremberg (DE); Anton Ebert, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 42 days.

(21) Appl. No.: 16/039,445

(22) Filed: Jul. 19, 2018

(65) Prior Publication Data
US 2019/0033977 A1 Jan. 31, 2019

(30) Foreign Application Priority Data
Jul. 25, 2017 (EP) .................................. 17183006

(51) Int. Cl.
*G06F 3/01* (2006.01)
*G06F 3/0485* (2013.01)
(Continued)

(52) U.S. Cl.
CPC ............. *G06F 3/017* (2013.01); *A61B 34/30* (2016.02); *A61B 34/74* (2016.02); *G06F 3/011* (2013.01);
(Continued)

(58) Field of Classification Search
CPC ...... G06F 3/017; G06F 3/011; G06F 3/04815; G06F 3/04845; G06F 3/0485;
(Continued)

(56) References Cited

U.S. PATENT DOCUMENTS

| | | |
|---|---|---|
| 2006/0187196 A1 | 8/2006 | Underkoffler et al. |
| 2014/0157206 A1 | 6/2014 | Ovsiannikov et al. |

(Continued)

FOREIGN PATENT DOCUMENTS

| | | |
|---|---|---|
| CN | 102402289 A | 4/2012 |
| CN | 106125925 A | 11/2016 |

(Continued)

OTHER PUBLICATIONS

Tecchia Franco et al: "I'm in VR!: using your own hands in a fully immersive MR system"; Virtual Reality Software and Technology; New York NY; USA; pp. 73-76; XP058061755; DOI: 10.1145/2671015.2671123; ISBN: 978-1-4503-3253-8.
(Continued)

*Primary Examiner* — Patrick N Edouard
*Assistant Examiner* — Joseph P Fox
(74) *Attorney, Agent, or Firm* — Harness, Dickey & Pierce, P.L.C.

(57) ABSTRACT

A method includes determining a first position of a thumb and a first position of an index finger at a first time; calculating a first distance between the thumb and the index finger at the first time based upon the first position of the thumb and index finger; determining a second position of the thumb and index finger at a second time, the second time being relatively later in time than the first time; calculating a second distance between the thumb and the index finger at the second time, based upon the second position of the thumb and index finger; identifying a pick-up gesture based upon the first distance and the second distance; selecting a first tool from a set of tools based upon a tool position of the first tool, the first tool being a real tool; and assigning the first tool to the pick-up gesture.

29 Claims, 6 Drawing Sheets

(51) Int. Cl.
*G06F 3/0484* (2013.01)
*G06F 3/0481* (2013.01)
*G06K 9/00* (2006.01)
*A61B 34/00* (2016.01)
*A61B 34/30* (2016.01)
*G06T 19/00* (2011.01)
*A61B 17/00* (2006.01)

(52) U.S. Cl.
CPC ........ *G06F 3/0485* (2013.01); *G06F 3/04815* (2013.01); *G06F 3/04845* (2013.01); *G06K 9/00355* (2013.01); *G06K 9/00389* (2013.01); *A61B 2017/00207* (2013.01); *A61B 2034/741* (2016.02); *G06K 9/00671* (2013.01); *G06T 19/006* (2013.01)

(58) Field of Classification Search
CPC ... A61B 34/30; A61B 34/74; A61B 2034/741; A61B 2017/00207; G06K 9/00389; G06K 9/00355; G06K 9/00671; G06T 19/006; G09B 7/00
See application file for complete search history.

(56) References Cited

U.S. PATENT DOCUMENTS

| | | |
|---|---|---|
| 2014/0368474 A1 | 12/2014 | Kim et al. |
| 2015/0234467 A1 | 8/2015 | Tachibana |
| 2016/0210781 A1 | 7/2016 | Thomas |
| 2017/0213473 A1* | 7/2017 | Ribeira ............... G06F 19/3456 |

FOREIGN PATENT DOCUMENTS

| | | |
|---|---|---|
| CN | 106960175 A | 7/2017 |
| EP | 2815699 A1 | 12/2014 |
| EP | 2908215 A1 | 8/2015 |

OTHER PUBLICATIONS

Extended European search report 17183006.0 dated Jan. 22, 2018.
Article 94 (3) Communication dated Oct. 30, 2019 in EP Application No. 17 183 006.0.
Chinese Office Action dated May 19, 2020 issued in Chinese Application No. 201810824493.9.

* cited by examiner

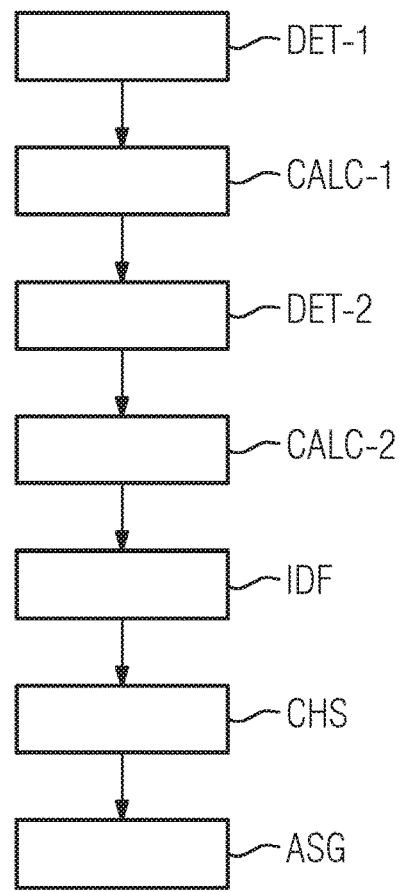
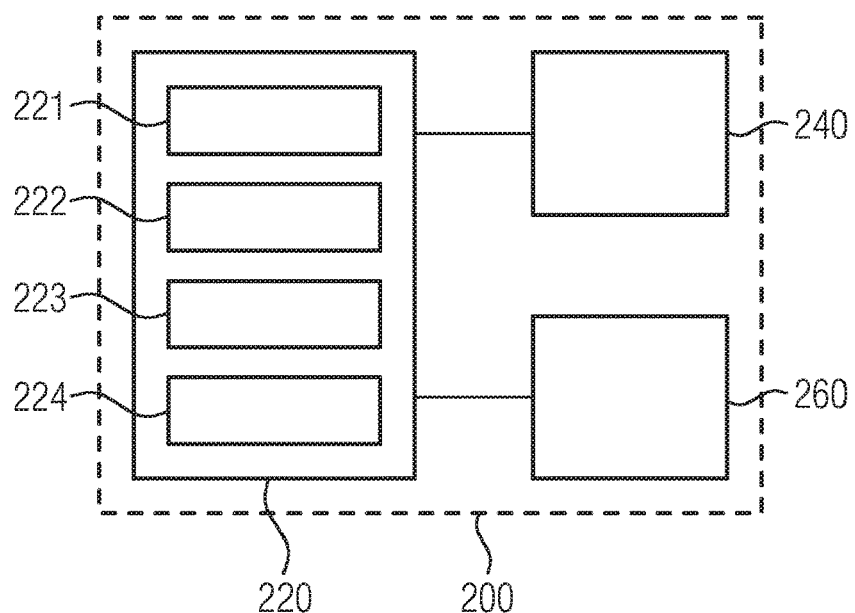

ASSIGNING A TOOL TO A PICK-UP GESTURE

PRIORITY STATEMENT

The present application hereby claims priority under 35 U.S.C. § 119 to European patent application number EP 17183006.0 filed Jul. 25, 2017, the entire contents of which are hereby incorporated herein by reference.

FIELD

At least one embodiment of the application is directed to a method, or an assignment system, for assigning a tool to a pick-up gesture.

BACKGROUND

In many fields of engineering, in particular in medical technology, the user performs training sessions for workflows not on the real object (e.g. the patient or a technical apparatus) but on training objects in virtual reality (VR), in mixed reality (MR) or in augmented reality (AR). Training sessions of this type can be monitored by sensors, and an automated assessment carried out, which can be used, for instance, for automated assessment of the success of the training or for adapting the training session to the requirements and powers of the user.

To facilitate an automated assessment, or even to present a training session in virtual, mixed or augmented reality, the correct version, or what is known as a prototype, of the workflow must be recorded. This is typically done by observing a user who has already been trained while the user performs the work sequence and/or by recording the movements of the user. In the case in which the prototypical workflow is translated into a training session in virtual reality, the tools used by the user during the prototypical workflow must be identified.

It is known in this context to use a visual recording of the workflow (e.g. a video) to assign the tools manually to times at which they were picked up by the trained user. A training session can then be generated based upon these times and the assigned tools.

SUMMARY

The inventors have discovered, however, that this manual process is time-consuming and prone to errors and, especially for small tools or when there are a large number of tools available, the visual recording of the workflow must also be of very high quality in order to identify the picked-up tools.

At least one embodiment of the invention therefore, during the recording of a training session, is directed to identifying in an automated manner, and hence in particular more quickly and more reliably, the tools used by a user during the prototypical workflow.

At least one embodiment is directed to a method for assigning a first tool; at least one embodiment is directed to a method for providing a sequence table for a user training session; at least one embodiment is directed to an assignment unit; at least one embodiment is directed to a provision unit; at least one embodiment is directed to a computer program product; and at least one embodiment is directed to a computer-readable storage medium. The description and the claims define advantageous developments.

The embodiments are described below both with reference to the claimed devices and with reference to the claimed method. Features, advantages or alternative embodiments mentioned in this connection can also be applied equally to the other claimed subject matter, and vice versa. In other words, the existing claims (which claims are directed at a device, for example) can also be developed by combining with features described or claimed in connection with a method. The corresponding functional features of the method are embodied in this case by corresponding physical modules or units.

The method according to at least one embodiment of the invention for assigning a first tool to a pick-up gesture is based on determining via a first position detector a first position of a thumb of a hand of a person and a first position of an index finger of the hand at a first time. In addition, a first distance between the thumb and the index finger at the first time is calculated via a processing unit based upon the first position of the thumb and the first position of the index finger. Furthermore, a second position of the thumb and a second position of the index finger at a second time, the second time being later in time than the first time, are determined via the first position detector. In addition, a second distance between the thumb and the index finger at the second time is calculated via the processing unit based upon the second position of the thumb and the second position of the index finger, the second time being later in time than the first time. In addition, a pick-up gesture is identified via the processing unit based upon the first distance and the second distance. Furthermore, a first tool is selected from a set of tools via the processing unit based upon a tool position of the first tool, the first tool being a real tool. In addition, the first tool is assigned to the pick-up gesture via the processing unit.

At least one embodiment of the invention also relates to a method for providing a sequence table for a user training session, the method comprising:

detecting movements of the person via a first position detector;

as a third determination, determining via a second position detector a set of tools with which a person can interact during the user training session;

as a second identification, identifying via a processing unit a pick-up gesture based upon the movement of a thumb of a hand of the person and of an index finger of the hand of the person;

selecting via the processing unit a first tool from the set of tools based upon a tool position of the first tool;

assigning the first tool to the pick-up gesture via the processing unit, providing via an interface a sequence table comprising at least one time of the pick-up gesture and the assigned tool.

At least one embodiment of the invention also relates to an assignment system for assigning a first tool to a pick-up gesture, which system comprises the following units:

a first position detector, designed for the first determination, which determines a first position of a thumb of a hand of a person and a first position of an index finger of the hand at a first time, also designed for the second determination, which determines a second position of the thumb and a second position of the index finger at a second time, the second time being later in time than the first time;

a processing unit, designed for the first calculation, which calculates a first distance between the thumb and the index finger at the first time based upon the first position of the thumb and the first position of the index finger, also designed for the second calculation, which calculates a second distance between the thumb and the index finger at the second time based upon the second position of the thumb and the second position of the index finger, also designed for the first identification, which identifies via the processing unit a pick-up gesture based upon the first distance and the second distance, also designed to select a first tool from a set of tools based upon a tool position of the first tool, also designed to assign the first tool to the pick-up gesture.

At least one embodiment of the invention can also relate to a provision system, which comprises the following units:

first position detector, designed to detect movements of a person;

second position detector, designed for the third determination, which determines a set of tools with which a person can interact during the user training session;

a processing unit, designed for the second identification, which identifies a pick-up gesture based upon the movement of a thumb of a hand of the person and of an index finger of the hand of the person, also designed to select a first tool from a set of tools based upon a tool position of the first tool, also designed to assign the first tool to the pick-up gesture;

interface for providing a sequence table comprising at least the assigned tool and the time of the pick-up gesture.

At least one embodiment of the invention also relates to a computer program product comprising a computer program and a computer-readable medium. An implementation largely in software has the advantage that even assignment systems already in use can be easily upgraded by a software update in order to work in the manner according to the invention. The computer program product may comprise in addition to the computer program, if applicable, extra elements such as e.g. documentation and/or extra components, and also hardware components such as e.g. hardware keys (dongles etc.) for using the software.

BRIEF DESCRIPTION OF THE DRAWINGS

The embodiments of the invention are described and explained in greater detail below with reference to pseudo-code and figures, in which:

FIG. 1 is a flow diagram of a method for assigning a pick-up gesture to a first tool;

FIG. 2 shows an assignment system;

DETAILED DESCRIPTION OF THE EXAMPLE EMBODIMENTS

Figure 3:
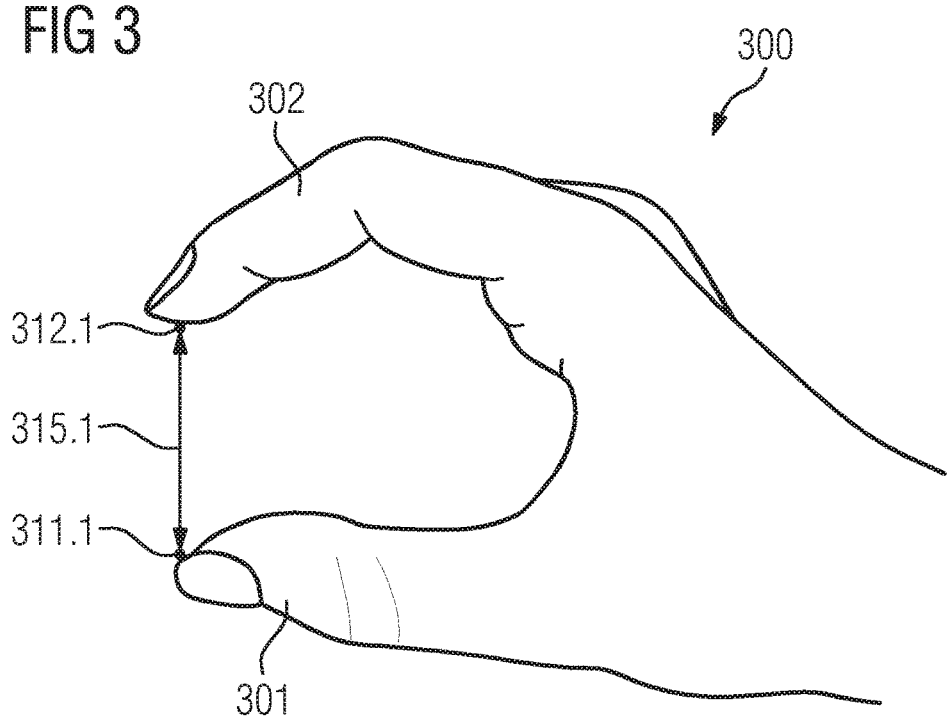
FIG. 3 shows a hand of a person at a first time.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for assigning a first tool to a pick-up gesture is based on determining via a first position detector a first position of a thumb of a hand of a person and a first position of an index finger of the hand at a first time. In addition, a first distance between the thumb and the index finger at the first time is calculated via a processing unit based upon the first position of the thumb and the first position of the index finger. Furthermore, a second position of the thumb and a second position of the index finger at a second time, the second time being later in time than the first time, are determined via the first position detector. In addition, a second distance between the thumb and the index finger at the second time is calculated via the processing unit based upon the second position of the thumb and the second position of the index finger, the second time being later in time than the first time. In addition, a pick-up gesture is identified via the processing unit based upon the first distance and the second distance. Furthermore, a first tool is selected from a set of tools via the processing unit based upon a tool position of the first tool, the first tool being a real tool. In addition, the first tool is assigned to the pick-up gesture via the processing unit.

The inventors have discovered that it is possible to recognize particularly easily that a person is taking hold of an object by detecting the position of thumb and index finger and by calculating the separation. If such a pick-up gesture or taking-hold process is registered based upon the separation, the tool that has been grasped can be selected from a set of tools particularly easily and quickly based upon the tool position and hence assigned to the pick-up position.

According to another possible embodiment of the invention, the first position and the second position of the thumb correspond to the coordinates of a singular point of the thumb, and also advantageously the first position and the second position of the index finger correspond to the coordinates of a singular point of the index finger. The first distance between thumb and index finger at the first time can then in particular correspond to the Euclidean distance of the first position of the thumb from the first position of the index finger; the second distance between thumb and index finger at the second time can then in particular correspond to the Euclidean distance of the second position of the thumb from the second position of the index finger.

According to another embodiment of the invention, the pick-up gesture is identified when the first distance is greater than a thumb/index-finger distance threshold value ("TI distance threshold value" for short) and when the second distance is less than or equal to the TI distance threshold value. The inventors have discovered that a pick-up gesture can be identified particularly easily and reliably when the separation of thumb and index finger drops below a TI distance threshold value. In particular, the TI distance threshold value can equal between 0.5 cm and 5 cm, in particular between 0.5 cm and 3 cm, in particular between 1 cm and 2.5 cm, in particular 2 cm. The inventors have discovered that a pick-up gesture can be identified particularly reliably using the TI distance threshold value.

According to another possible embodiment of the invention, the time interval between the first time and the second time is less than 2 seconds ("2 s" for short), in particular less than 1 s, in particular less than 100 milliseconds ("100 ms" for short), in particular less than 10 ms. The time interval between the first time and the second time can equal in particular the inverse of the sampling frequency of the first position detector. The inventors have discovered that the pick-up gesture can be recognized particularly reliably by such a choice of time interval because a pick-up movement or pick-up gesture of the person can be inferred very reliably from such a change in position between thumb and index finger in such a time interval.

According to another possible embodiment of the invention, the selection is also based on a hand position, the hand position relating to the position of the hand of the person at a third time. The hand position can be based in particular on the first position of the thumb and/or on the first position of the index finger. The hand position can be based in particular on the second position of the thumb and/or on the second position of the index finger. The hand position can also be identical to the first position of the thumb, the second position of the thumb, the first position of the index finger or the second position of the index finger. The third time in particular can equal the first time or the second time; in addition the third time can also lie between the first time and the second time. The third time can also be referred to as the pick-up gesture time. The inventors have discovered that the first tool can be selected particularly reliably and with few errors based upon the hand position.

According to another possible embodiment of the invention, a second tool is also selected from the set of tools via the processing unit based upon a tool position of the second tool. In addition, the second tool is assigned to the pick-up gesture via the processing unit. The inventors have discovered that by selecting and assigning a plurality of tools to one pick-up gesture, it is less common for tools that the person does not pick up at all to be assigned, in particular when tools are closely spaced. By assigning a first tool and a second tool, the method is therefore less prone to errors.

According to another embodiment of the invention, the selection is also based on the first position of the thumb and/or on the first position of the index finger, or the selection is based on the second position of the thumb and/or on the second position of the index finger. In particular the selection can be based on the first position of the thumb, in particular the selection can be based on the first position of the index finger, in particular the selection can be based both on the first position of the thumb and on the first position of the index finger. In particular the selection can be based also on the second position of the thumb, in particular the selection can be based on the second position of the index finger, in particular the selection can be based both on the second position of the thumb and on the second position of the index finger. The inventors have discovered that it is possible to select the first tool particularly quickly and efficiently by using the position of the thumb and/or of the index finger at the first time.

According to another embodiment of the invention, the first tool is selected such that the distance of the tool position from the second position of the thumb and/or from the second position of the index finger is less than a finger/tool distance threshold value ("FT distance threshold value" for short). The inventors have discovered that the first tool can be selected particularly easily and quickly by using a threshold value for the distance.

According to another possible embodiment of the invention, the first tool is selected such that the distance of the tool position from the first position of the thumb and/or from the first position of the index finger is less than a finger/tool distance threshold value ("FT distance threshold value" for short). The inventors have discovered that the first tool can be selected particularly easily and quickly by using a threshold value for the distance.

According to another embodiment of the invention, exactly one first tool is selected, wherein the distance of the first tool from the second position of the thumb or from the second position of the index finger is less than or equal to the distance of every tool of the set of tools from the second position of the thumb or from the second position of the index finger. In particular, the distance of the first tool from the second position of the thumb can be less than or equal to the distance of every tool of the set of tools from the second position of the thumb. In particular, the distance of the first tool from the second position of the index finger can be less than or equal to the distance of every tool of the set of tools from the second position of the index finger. The inventors have discovered that by selecting the first tool in this way, the selection is particularly fast and simple because a picked-up tool generally is close to thumb and index finger of the hand performing the picking-up.

According to another possible embodiment of the invention, the tool position is determined via a second position detector based upon a tool position marker, wherein the tool position marker is arranged on the first tool. The inventors have discovered that the tool position can be determined particularly easily and accurately via a tool position marker. The second position detector in particular can be identical to the first position detector, although the second position detector in particular can also be different from the second position detector.

According to another possible embodiment of the invention, the tool position marker comprises an RFID transponder, and the second position detector comprises an RFID reader. RFID is an acronym for "Radio Frequency IDentification" here. In particular, the RFID reader can also be arranged on the hand of the person. The inventors have discovered that tools can be recognized and selected particularly accurately and easily by using a system comprising an RFID transponder and an RFID reader.

According to another embodiment of the invention, the tool position is determined via a visual imaging system. In this case, the tool position is based on at least one visual image from the visual imaging system. In particular, the tool position can also be based on two visual images from the visual imaging system, the two visual images having been acquired from different directions. In particular, the tool position can also be based on three visual images from the visual imaging system, the three visual images having been acquired from three different pairs of directions. The inventors have discovered that by using a visual imaging system, the tools of the set of tools do not need to be modified, so in particular there is no need to attach a tool position marker. This means that the method can be implemented at lower cost.

According to another embodiment of the invention, the first tool is selected from a subset of the set of tools, wherein every tool of the subset is at a distance from the person that is less than a person/tool distance threshold value ("PT distance threshold value" for short). The distance of one of the tools from the position is in particular the distance of the tool from a singular point of the person, for example from the center of the body of the person. The PT distance threshold value may be in particular less than 100 cm, in particular less than 50 cm, in particular even less than 20 cm. The inventors have discovered that such a restriction can reduce the basic set from which the first tool is selected. This reduces the processing time required and/or speeds up the method.

According to another embodiment of the invention, the first position detector comprises a visual imaging system, wherein for the first determination, a first visual image is acquired, and the first position of the thumb and/or the first position of the index finger is determined based upon the first visual image, and wherein furthermore for the second determination, a second visual image is acquired, and the second position of the thumb and/or the second position of the index finger is determined based upon the second visual image. The inventors have discovered that by using a visual imaging system, only slight modifications need to be made to the person. This results in lower costs, and also means that there is no technical equipment attached to the person to bother the person during the recording of a training session.

According to another embodiment of the invention, a first position marker is arranged on the thumb, and a second position marker is arranged on the index finger. The first and second positions of the thumb are thereby determined by locating the first position marker, and the first and second positions of the index finger are determined by locating the second position marker. In particular, the first position of the thumb can be identified by the position of the first position marker at the first time, and the second position of the thumb can be identified by the position of the first position marker at the second time. In particular, in addition the first position of the index finger can be identified by the position of the second position marker at the first time, and the second position of the index finger can be identified by the position of the second position marker at the second time. The inventors have discovered that the positions of thumb and index finger can be determined particularly accurately by using position markers. The inventors have discovered that it is thereby possible not only to determine the distance between thumb and index finger particularly accurately but also to determine the distance from thumb or index finger to a tool particularly accurately.

According to another embodiment of the invention, the first position detector comprises a visual imaging system, wherein the first position marker and the second position marker are located in a visual image. The combination of visual imaging system and the first and second position markers may be in particular a motion capture system. The inventors have discovered that the positions of thumb and index finger can be determined both accurately and at low cost by using such a system, because in particular there is no need to fit any active components for the position markers.

At least one embodiment of the invention also relates to a method for providing a sequence table for a user training session, the method comprising:
  detecting movements of the person via a first position detector;
  as a third determination, determining via a second position detector a set of tools with which a person can interact during the user training session;
  as a second identification, identifying via a processing unit a pick-up gesture based upon the movement of a thumb of a hand of the person and of an index finger of the hand of the person;
  selecting via the processing unit a first tool from the set of tools based upon a tool position of the first tool;
  assigning the first tool to the pick-up gesture via the processing unit, and
  providing via an interface a sequence table comprising at least one time of the pick-up gesture and the assigned tool.

The inventors have discovered that a user training session can be created particularly easily and quickly by the provided sequence table because the tools picked up by the person no longer need to be captured manually.

According to another embodiment of the method for providing a sequence table, the pick-up gesture is identified based upon a first distance between thumb and index finger at a first time, and on a second distance between thumb and index finger at a second time, where the second time is later in time than the first time, and where the time of the pick-up gesture lies between the first time and the second time. The inventors have discovered that a first identification based on separations of thumb and index finger can be performed particularly easily and accurately.

According to another possible embodiment of the invention, the first tool is in addition selected based upon the hand position of the hand. The hand position in this case can be based in particular on the position of the thumb or of the index finger, in particular on the positions at the first time and/or at the second time. The inventors have discovered that the first tool can be selected particularly easily and accurately based upon the hand position.

According to another embodiment of the method for providing a sequence table, the method step of the second identification comprises the following method steps of the method for assigning a first tool:
- as a first determination, determining via a first position detector a first position of a thumb of a hand of a person and a first position of an index finger of the hand at a first time;
- as a first calculation, calculating via the processing unit a first distance between the thumb and the index finger at the first time based upon the first position of the thumb and the first position of the index finger;
- as a second determination, determining via the first position detector a second position of the thumb and a second position of the index finger at a second time, the second time being later in time than the first time;
- as a second calculation, calculating via the processing unit a second distance between the thumb and the index finger at the second time based upon the second position of the thumb and the second position of the index finger;
- as a first identification, identifying via the processing unit a pick-up gesture based upon the first distance and the second distance.

The inventors have discovered that the sequence table can be created particularly easily and reliably by this embodiment of the second identification.

According to another embodiment of the method for providing a sequence table, the method steps are developed analogously to the method for assigning a first tool. In particular, a step of the method for providing a sequence table, which corresponds to a step of the method for assigning a first tool, can be developed by features of the description of the method for assigning a first tool and by dependent claims referring back to the method for assigning a first tool. Corresponding advantages shall be applied analogously.

At least one embodiment of the invention also relates to an assignment system for assigning a first tool to a pick-up gesture, which system comprises the following units:
- a first position detector, designed for the first determination, which determines a first position of a thumb of a hand of a person and a first position of an index finger of the hand at a first time,
also designed for the second determination, which determines a second position of the thumb and a second position of the index finger at a second time, the second time being later in time than the first time;
- a processing unit, designed for the first calculation, which calculates a first distance between the thumb and the index finger at the first time based upon the first position of the thumb and the first position of the index finger,
also designed for the second calculation, which calculates a second distance between the thumb and the index finger at the second time based upon the second position of the thumb and the second position of the index finger,
also designed for the first identification, which identifies via the processing unit a pick-up gesture based upon the first distance and the second distance,
also designed to select a first tool from a set of tools based upon a tool position of the first tool, also designed to assign the first tool to the pick-up gesture.

The assignment system can be designed in particular to perform the above-described methods according to the invention and aspects thereof. The assignment system is designed to perform these methods and aspects thereof by the first position detector and the processing unit being designed to perform the relevant method steps.

At least one embodiment of the invention can also relate to a provision system, which comprises the following units:
- first position detector, designed to detect movements of a person;
- second position detector, designed for the third determination, which determines a set of tools with which a person can interact during the user training session;
- a processing unit, designed for the second identification, which identifies a pick-up gesture based upon the movement of a thumb of a hand of the person and of an index finger of the hand of the person,
also designed to select a first tool from a set of tools based upon a tool position of the first tool,
also designed to assign the first tool to the pick-up gesture;
- interface for providing a sequence table comprising at least the assigned tool and the time of the pick-up gesture.

At least one embodiment of the invention also relates to a computer program product comprising a computer program and a computer-readable medium. An implementation largely in software has the advantage that even assignment systems already in use can be easily upgraded by a software update in order to work in the manner according to the invention. The computer program product may comprise in addition to the computer program, if applicable, extra elements such as e.g. documentation and/or extra components, and also hardware components such as e.g. hardware keys (dongles etc.) for using the software.

The hand position is in particular the position of a singular point on the hand. The hand position can be based in particular on the first position of the thumb and/or of the index finger, or alternatively on the second position of the thumb and/or of the index finger.

The tool position of a first tool and/or of a second tool is in particular the position of a singular point on the first tool and/or on the second tool.

The first position (of the thumb and/or of the index finger), the second position (of the thumb and/or of the index finger), the hand position and/or the tool position can be characterized in this case by three-dimensional coordinates of the singular point with respect to a reference coordinate system. In addition, the first position and/or the second position of the thumb can also include an orientation of the thumb, in addition the first position and/or the second position of the index finger can also include an orientation of the index finger, in addition the hand position can also include an orientation of the hand, in addition the tool position can also include an orientation of the tool. The orientation can be defined by three-dimensional coordinates (of a vector) with respect to the reference coordinate system.

The tool position can also in particular be given by a singular point of a tool position marker, the tool position marker being arranged on the tool. The singular point of the tool position marker may be in particular the center of the tool position marker.

The first position (of the thumb and/or of the index finger), the second position (of the thumb and/or of the index finger), the hand position and/or the tool position can also be defined relative to another point in the reference coordinate system. In particular, the first position (of the thumb and/or of the index finger), the second position (of the thumb and/or of the index finger), the hand position and/or the tool position can also involve just a piece of information on the associated distance to the other point.

A first position marker, a second position marker and/or a tool position marker is in particular an active position marker or a passive position marker. An active position marker can emit in particular radiation that allows the position of the active position marker to be found. Radiation can involve in particular electromagnetic radiation, and in this case can denote in particular light or radio signals. RFID transponders or Bluetooth beacons are examples of active position markers; colored spheres are an example of a passive position marker.

A visual imaging system may be in particular a camera or a plurality of cameras, which use light in the visible spectrum to generate image data. The image data object may be in particular two-dimensional and/or three-dimensional image data. In particular when there are a plurality of cameras capturing an object from a plurality of directions, a coordinate in the three-dimensional space can be assigned to image points of the image data.

In particular in this context, the bringing together and/or closing of thumb and index finger of a hand of a person denotes a pick-up gesture, irrespective of whether a tool or another object is actually picked up. A pick-up gesture time and a pick-up gesture position can be assigned to a pick-up gesture.

FIG. 1 shows a flow diagram of a method for assigning a pick-up gesture to a first tool 601, 602, 603. The first step of the method shown in FIG. 1 is the first determination DET-1, which determines via a first position detector 240 a first position 311.1 of a thumb 301 of a hand 300 of a person 701 and a first position 312.1 of an index finger 302 of the hand 300 at a first time. In the example embodiment shown, a first position marker 321 is arranged on the thumb 301, and a second position marker 322 is arranged on the index finger 302. The first position marker 321 and the second position marker 322 are both spherical objects of a different color from the color of the hand 300, for instance white in color.

Figure 7:
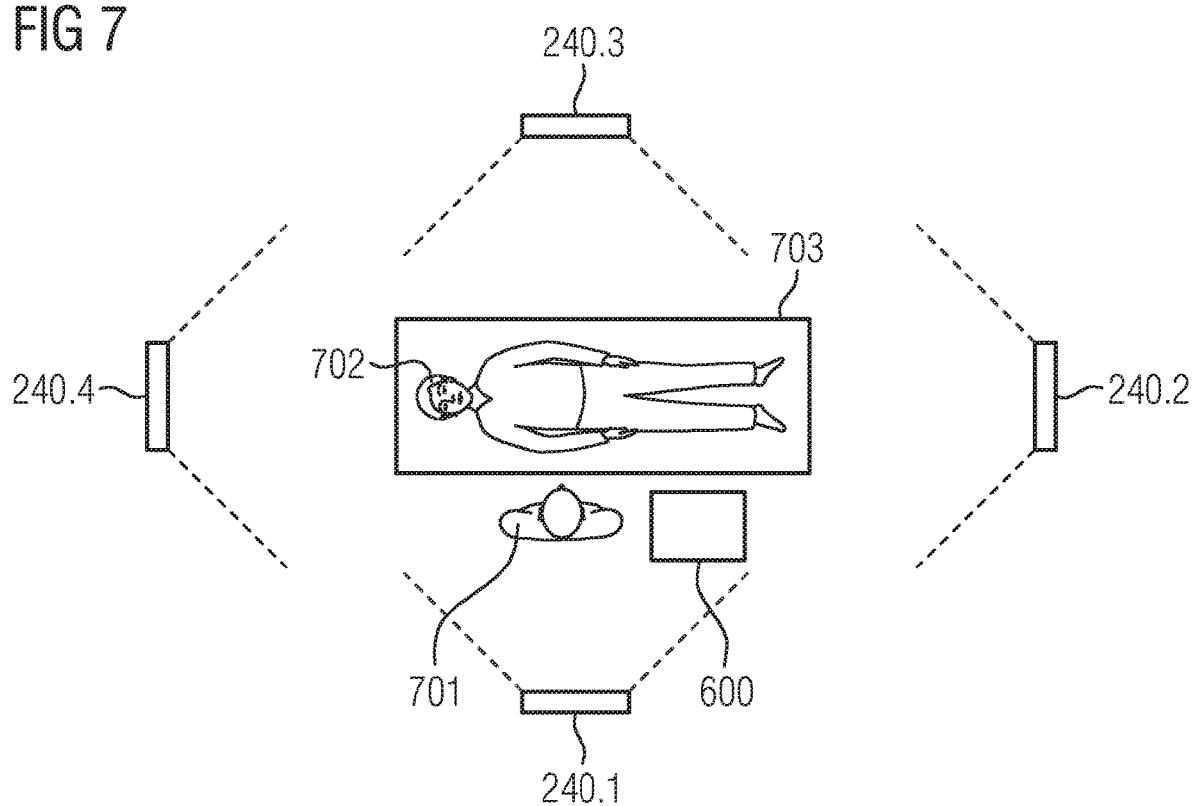
FIG. 7 is a schematic diagram showing a bird's eye view of the setup for performing the method.

In the example embodiment shown, the first position detector 240 is a system composed of a plurality of position detector subunits 240.1, . . . , 240.4, where each of the position detector subunits 240.1, . . . , 240.4 is a visual imaging system, for instance a camera, that is designed to acquire images in the visual spectrum. The position detector subunits 240.1, . . . , 240.4 are arranged such that the hand 300 and hence the position markers 321, 322 can be imaged from a plurality of directions, and hence the three-dimensional coordinates of the position markers 321, 322 can be determined from the two-dimensional image data from the position detector subunits 240.1, . . . , 240.4. FIG. 7 shows an example of an arrangement of the position detector subunits 240.1, . . . , 240.4. Alternatively, separate position markers 321, 322 can be dispensed with; in this case, image recognition is used to locate in the images characteristic structures (e.g. the fingernail or the tip) of the thumb 301 or of the index finger 302, and the three-dimensional position of these characteristic structures is determined.

In the example embodiment shown, the first position 311.1 of the thumb 301 is identified by the center of the first position marker 321 at the first time. In addition, the first position 312.1 of the index finger 302 is identified by the center of the first position marker 322 at the first time. The first position 311.1 of the thumb 301 and the first position 312.1 of the index finger 302 hence each correspond to a coordinate tuple, in particular a three-dimensional coordinate tuple.

The second step of the method shown in FIG. 1 is the first calculation CALC-1, which calculates via a processing unit 222 a first distance 315.1 between the thumb 301 and the index finger 302 at the first time based upon the first position 311.1 of the thumb 301 and the first position 312.1 of the index finger 302. In the example embodiment shown, the first distance 315.1 is calculated as a Euclidean distance of the first position 311.1 of the thumb 301 from the first position 312.1 of the index finger 302, in other words as:

$$\text{dist}(x,y) := \sqrt{(x_1-y_1)^2+(x_2-y_2)^2+(x_3-y_3)^2}$$

where x denotes the first position 311.1 of the thumb 301 and y the first position 312.1 of the index finger 302, and where $x_i$ and $y_i$ denote the i-th element of the respective coordinate tuples.

The third step of the method shown in FIG. 1 is the second determination DET-2, which determines via the first position detector 240 a second position 311.2 of the thumb 301 and a second position 312.2 of the index finger 302 at a second time, the second time being later in time than the first time. The second determination DET-2 is advantageously designed to be similar to the first determination DET-1 of the example embodiment shown. The time interval between the first time and the second time can be chosen to be 0.1 seconds, for example, or other time intervals are alternatively possible of course.

In the example embodiment shown, the second position 311.2 of the thumb 301 is in particular identified by the center of the first position marker 321 at the second time. In addition, the second position 312.2 of the index finger 302 is identified by the center of the first position marker 322 at the second time. The second position 311.2 of the thumb 301 and the second position 312.2 of the index finger 302 hence correspond to a coordinate tuple, in particular a three-dimensional coordinate tuple.

In an alternative example embodiment of the method, it is also possible to perform the first calculation CALC-1 later in time than the second determination DET-2, and it is equally possible to perform the first calculation CALC-2 at the same time as the second determination DET-2. The step of the second determination DET-2 is independent of the step of the first calculation CALC-1.

The fourth step of the method shown in FIG. 1 is the second calculation CALC-2, which calculates via the processing unit 222 a second distance 315.2 between the thumb 301 and the index finger 302 at the second time based upon the second position 311.2 of the thumb 301 and the second position 312.2 of the index finger 302. In the example embodiment shown, the second distance 315.2 is calculated as the Euclidean distance of the second position 311.2 of the thumb 301 from the second position 312.2 of the index finger 302.

The fifth step of the example embodiment shown in FIG. 1 is the first identification IDF-1, which identifies via the processing unit 222 a pick-up gesture based upon the first distance 315.1 and the second distance 315.2. In the example embodiment shown, a pick-up gesture is identified when the first distance 315.1 is greater than a TI distance threshold value and when the second distance 315.2 is less than or equal to the TI distance threshold value. In other words, a pick-up gesture is identified when the distance between thumb 301 and index finger 302 drops below the TI distance threshold value. A typical and suitable TI distance threshold value is 2 cm, although obviously other TI distance threshold values can also be used. The TI distance threshold value can advantageously also be adjusted to suit the size of the hand 300 of the person 701.

The sixth step of the example embodiment of the method shown in FIG. 1 is selecting CHS a first tool 601, 602, 603 from a set of tools via the processing unit 222 based upon a tool position of the first tool 601, 602, 603. In the example embodiment shown, the tool position of a tool 601, 602, 603 is the position of the tool 601, 602, 603 at the second time. Alternatively, it is also possible to select the tool position of a tool 601, 602, 603 to be the position of the tool 601, 602, 603 at the first time. In addition, it is also possible alternatively to select the tool position of a tool 601, 602, 603 to be the position of the tool 601, 602, 603 at a different time, between the first time and the second time, in particular at the halfway point in time between the first time and the second time.

Figure 6:
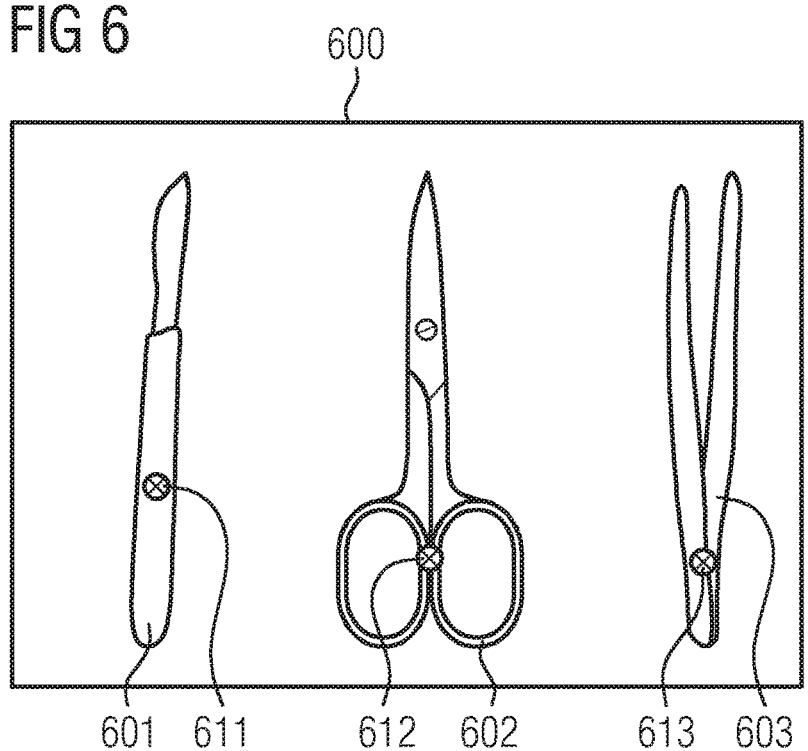
FIG. 6 shows a tool table comprising tools.

In this example embodiment, on each of the tools 601, 602, 603 is arranged an associated RFID transponder as a tool position marker 611, 612, 613, the position of which can be determined by an RFID reader as a second position detector 260. Reference is made to FIG. 6, which gives a specific description.

In the example embodiment shown, the tool 601, 602, 603 for which the tool position is at a minimum distance from the second position 311.2 of the thumb 301 is selected from the set of tools.

The seventh step of the example embodiment of the method shown in FIG. 1 is assigning ASG the first tool 601, 602, 603 to the pick-up gesture via the processing unit 222. In the example embodiment shown, this is done by storing in a sequence table and/or a database an assignment between the time of the pick-up gesture and a tool dataset 1021.1, . . . , 1021.M. Optionally, additional data can also be saved in this sequence table and/or database, for instance the hand position and/or the tool position at the time of the pick-up gesture.

These assignments of one or a plurality of first tools 601, 602, 603 to pick-up gestures can then be used to provide a desired sequence for a user training session.

FIG. 2 shows an assignment system 200 comprising a first position detector 240 and an assignment unit 220. The assignment system 200 shown here is designed to perform the method according to the invention. The assignment system 200 can optionally also comprise a second position detector 260. The assignment unit 220 and the first position detector 240 and the optional second position detector 260 are connected to one another for the purpose of data transfer, which connection may be a network connection (e.g. a local area network, or LAN for short, via Ethernet, a wireless local area network, or WLAN for short), a connection via universal serial bus (USB) or other known connections for connecting peripheral devices to computers.

The assignment unit 220 comprises an interface 221, a processing unit 222, a memory unit 223 and an input/output unit 224. The assignment unit 220 may be in particular a computer, a microcontroller or an integrated circuit. Alternatively, the assignment unit 220 is a real or virtual interconnection of computers (a real interconnection is referred to as a "cluster" and a virtual interconnection is referred to as a "cloud"). An interface 221 may be a hardware or software interface (for instance PCI bus, USB or firewire). A processing unit 222 may comprise hardware elements or software elements, for instance a microprocessor or what is known as a field programmable gate array (FPGA). A memory unit 223 may be implemented as a non-permanent main memory (random access memory or RAM for short) or as a permanent mass storage device (hard disk, USB stick, SD card, solid state disk). An input/output unit 224 comprises at least one input unit and/or at least one output unit.

In the example embodiment shown, the first position detector 240 is a system composed of a plurality of position detector subunits 240.1, . . . , 240.4, where each of the position detector subunits 240.1, . . . , 240.4 is a visual imaging system, for instance a camera, that is designed to acquire images in the visual spectrum. This first position detector 240 has already been described in detail above.

In addition in the example embodiment shown, the second position detector 260 is an RFID reader, which can receive and process signals from RFID transponders. For the purpose of determining the tool position, a tool position marker 611, 612, 613 in the form of an RFID transponder is formed on the available tools 601, 602, 603.

Alternatively, the second position detector 260 can obviously also be formed, similar to the first position detector 240 of this example embodiment, by a plurality of visual imaging systems; likewise, the first position detector 240 can alternatively be in the form of an RFID reader.

In addition, also other embodiments are alternatively possible also for the first position detector 240 and/or the second position detector 260, for instance embodiments based on Bluetooth beacons as the tool position markers 611, 612, 613, advantageously using the "Bluetooth Low Energy" technology, or based on other transmit and receive mechanisms for electromagnetic waves, in particular radio waves.

The second position detector 260 may also be identical to the first position detector 240 if the positions of thumb 301 and index finger 302 are determined in a similar way to determining a tool position.

If the optional second position detector 260 is not present, the tool position of each of the tools 601, 602, 603 can be established in advance and stored in the memory unit 223. This is advantageous, for example, when the tools 601, 602, 603 are arranged in defined spatial positions before recording the user training session, and the person 701 places tools 601, 602, 603 back in the initial position after use. This is the case in medical applications, for example, in which the surgical instruments are placed in a defined arrangement on the tool table 600.

Figure 4:
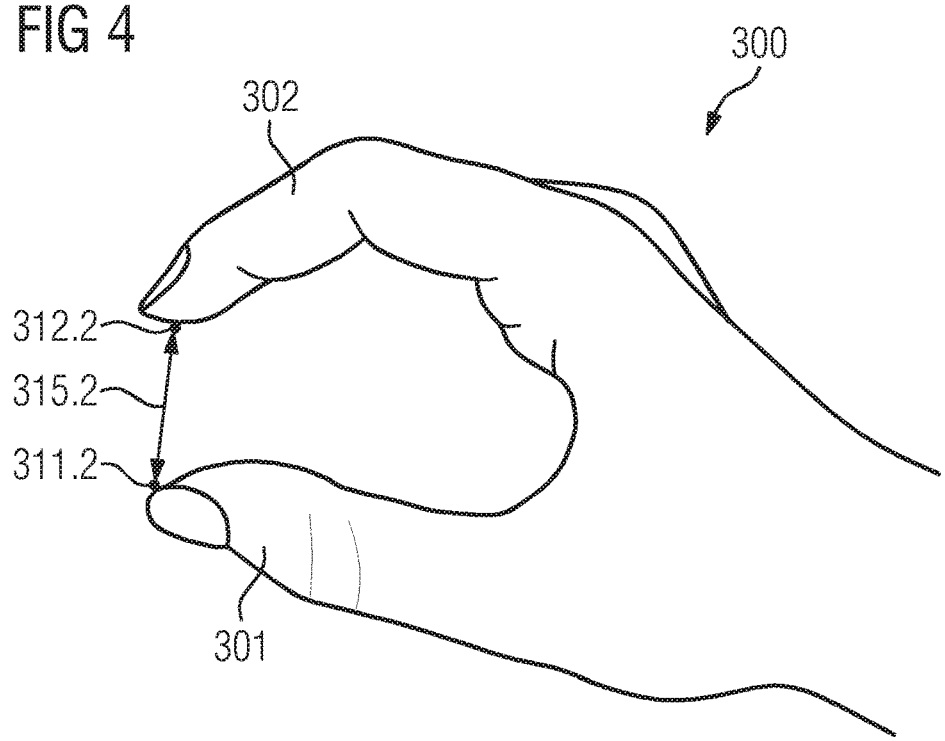
FIG. 4 shows the hand of the person at a second time.

FIG. 3 shows a view of a hand 300 of a person 701 at a first time; FIG. 4 shows a view of the hand 300 of the person 701 at a second time. The hand 300 comprises a thumb 301 and an index finger 302. FIG. 3 also shows the first position 311.1 of the thumb 301 and the first position 312.1 of the index finger 302, where the first position 311.1 of the thumb 301 is the position of the thumb 301 at the first time, and where the first position 312.1 of the index finger 302 is the position of the index finger 302 at the first time; in addition the figure shows the first distance 315.1 between the first position 311.1 of the thumb 301 and the first position 312.1 of the index finger 302. In addition, FIG. 4 shows the second position 311.2 of the thumb 301 and the second position 312.2 of the index finger 302, where the second position 311.2 of the thumb 301 is the position of the thumb 301 at the second time, and where the second position 312.2 of the index finger 302 is the position of the index finger 302 at the second time; in addition the figure shows the second distance 315.2 between the second position 311.2 of the thumb 301 and the second position 312.2 of the index finger 302.

In the example embodiment shown in FIG. 3 and FIG. 4, the first position 311.1 of the thumb 301 is given by a singular point of the thumb 301, in this case the edge of the thumb nail. The second position 311.2 of the thumb 301 is given by the same singular point. In addition, the first position 312.1 of the index finger 302 is likewise given by a singular point, in this case the center of the fingertip. The second position 312.2 of the index finger 302 is given by the same singular point. The first distance 315.1 in this embodiment equals the Euclidean distance between the first position 311.1 of the thumb 301 and the first position 312.1 of the index finger 302. The second distance 315.2 in this embodiment equals the Euclidean distance between the second position 311.2 of the thumb 301 and the second position 312.2 of the index finger 302.

Figure 5:
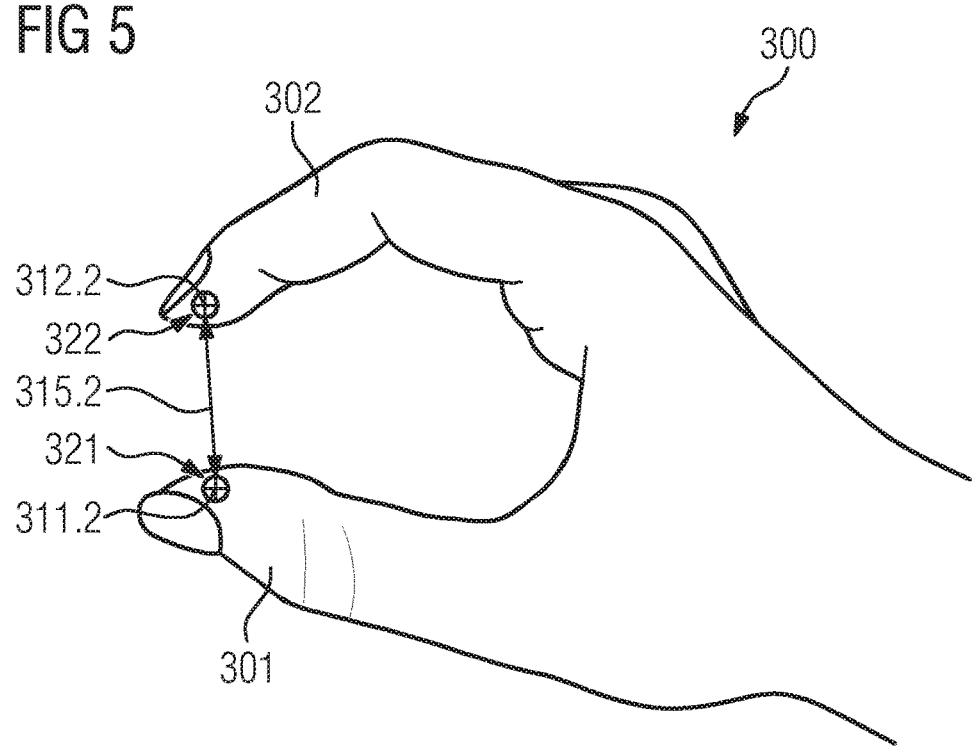
FIG. 5 shows a hand of a person having position markers.

FIG. 5 shows the hand 300 of a person 701 in an example embodiment using a first position marker 321 and a second position marker 322. In this embodiment, the first position marker 321 is arranged on the thumb 301, and the second position marker 322 is arranged on the index finger 302. In this example embodiment, the first position 311.1 and the second position 311.2 of the thumb 301 are each given by the position of the center of the first position marker 321, the first position 312.1 and second position 312.2 of the index finger 302 are given by the position of the center of the second position marker 322.

In the example embodiment shown, the first position marker 321 and the second position marker 322 are visual markers by way of a small sphere, which is of contrasting color from the hand 300 of the person 701 and therefore can be recognized easily in a visual image. Alternatively, a visual marker can also be implemented by marking that is not discernible in the visible spectrum (e.g. color that reflects in the ultraviolet or infrared portion of the spectrum), or by a defined color pattern, or also alternatively can emit light. If the first position marker 321 and/or the second position marker 322 has no rotational symmetry about at least one axis of rotation, the position and orientation of the particular position marker can even be determined based upon fewer visual images.

FIG. 6 shows a tool table 600 comprising tools 601, 602, 603. The tools 601, 602, 603 are medical/surgical instruments, depicted in the figure as a scalpel 601, a pair of scissors 602 and a pair of forceps 603. A tool position marker 611, 612, 613 is arranged on all the tools 601, 602, 603 shown. In this example embodiment, the tool position marker 611, 612, 613 is an RFID transponder. The tool position markers 611, 612, 613 in this example embodiment are arranged close to the regions at which the tools 601, 602, 603 are typically picked up by the hand 300. The position or the coordinates of the tool position markers 611, 612, 613 are determined in this example embodiment by the second position detector 260, which is an RFID reader.

Alternatively, also a plurality of tool position markers 611, 612, 613 can be arranged on one or more of the tools 601, 602, 603. The position of the tool 601, 602, 603 is defined in this case by the position of one of the tool position markers 611, 612, 613 arranged on the tool 601, 602, 603. Using a plurality of tool position markers 611, 612, 613 is advantageous especially for large tools 601, 602, 603 and for multifunctional tools 601, 602, 603. In particular it is possible when using a plurality of tool position markers 611, 612, 613 to determine the orientation of the tool 601, 602, 603 just based upon the coordinates of the tool position markers 611, 612, 613.

FIG. 7 shows a plan view of an arrangement for recording an assignment between pick-up gestures 1001.1, . . . , 1001.N and tools 601, 602, 603. The figure shows the person 701 whose movements and tool pick-up actions are recorded and translated into a training session. The figure also shows a patient support apparatus 703 comprising a patient 702.

The patient 702 may be a real person; in addition the patient may alternatively be a mock person. In addition, the patient 702 may alternatively also be merely depicted for the person 701 in virtual reality, in mixed reality or in augmented reality via a viewing device of the person 701. FIG. 6 also shows a tool table 600, placed on which are tools 601, . . . , 603. The tool table 600 and the tools 601, . . . , 603 may again be real tools, mock tools or depictions for the person 701 in virtual reality, in mixed reality or in augmented reality via a viewing device of the person 701. In the example embodiment shown, the position detector 240 comprises four individual detector subunits 240.1, . . . , 240.4; this multiplicity of detector subunits 240.1, . . . , 240.4 can be used for good detection of the positions of the hand 300 or of the thumb 301 and of the index finger 302. Alternatively and equivalently, other quantities and arrangements of detector subunits 240.1, . . . , 240.4 can also be used.

Figure 8:
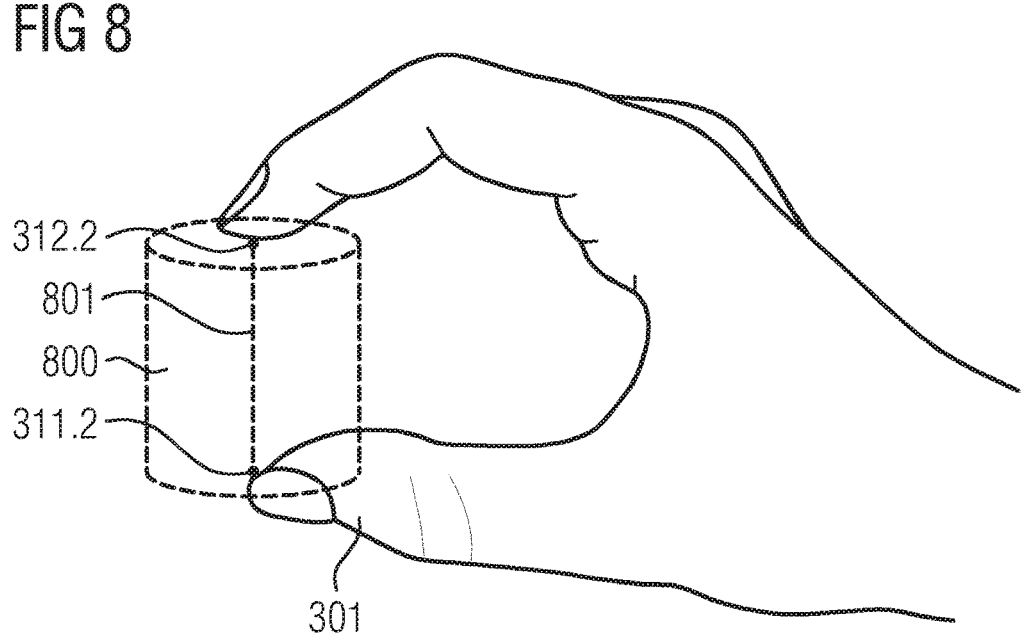
FIG. 8 shows a first example embodiment of a region of tool positions that can be assigned to a pick-up gesture.
Figure 9:
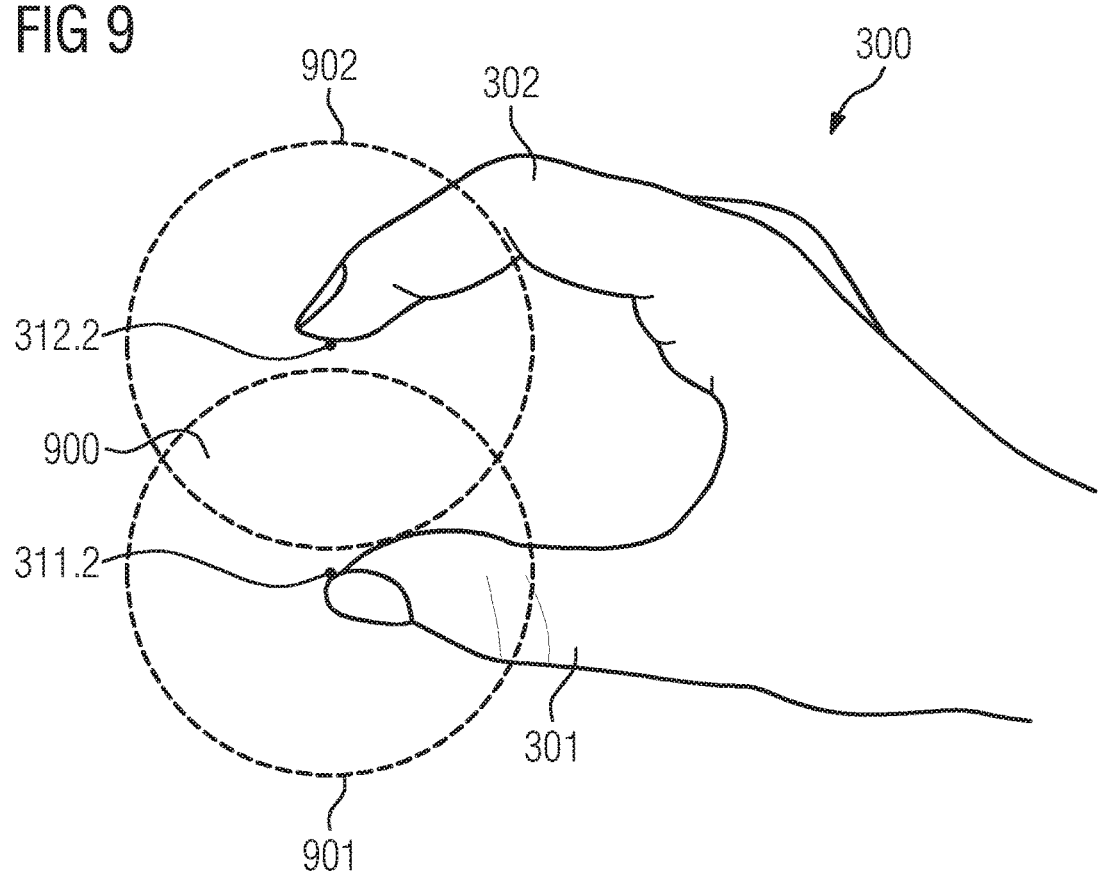
FIG. 9 shows a second example embodiment of a region of tool positions that can be assigned to a pick-up gesture.

FIG. 8 shows a first example embodiment of a region 800 of tool positions that can be assigned to a pick-up gesture; FIG. 9 shows a second example embodiment of a region 900 of tool positions that can be assigned to a pick-up gesture.

The region 800 of the first example embodiment is defined as a cylinder, the main axis of which corresponds to the line 801 between the second position 311.2 of the thumb 301 and the second position 312.2 of the index finger 302. A first tool 601, 602, 603 is thus assigned to a pick-up gesture if, at the time of the pick-up gesture, the tool position is arranged inside the cylinder. In other words, a first tool 601, 602, 603 is assigned to the pick-up gesture if, at the time of the pick-up gesture, the tool position is at a distance from the line 801 between the second position 311.2 of the thumb 301 and the second position 312.2 of the index finger 302 that is less than a defined distance threshold value, and is at a distance from the second position 311.2 of the thumb 301 that is greater than or equal to the distance from the line 801, and is at a distance from the second position 312.2 of the index finger 302 that is greater than or equal to the distance from the line 801.

The region 900 of the first example embodiment is defined as the set of all the points that are at a distance from the second position 311.2 of the thumb 301 that is less than a defined distance threshold value, and are simultaneously at a distance from the second position 312.2 of the index finger 302 that is less than the defined distance threshold. In this case the region 900 therefore corresponds to the volume of intersection of a first sphere 901 and a second sphere 902, where the first sphere 901 is a sphere about the second position 311.2 of the thumb 301, where the second sphere 902 is a sphere about the second position 312.2 of the index finger 302, and where the first sphere 901 and the second sphere 902 have a radius that equals the defined distance threshold value.

Figure 10:
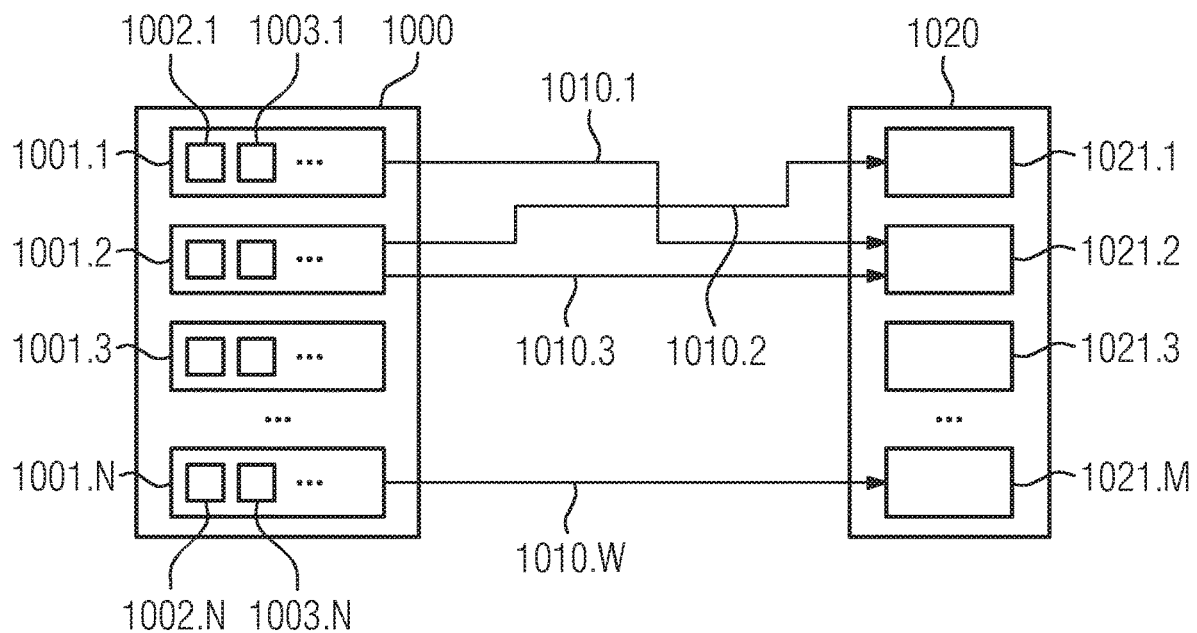
FIG. 10 shows an assignment table that assigns pick-up gestures to tools.

FIG. 10 shows an assignment between pick-up gesture datasets 1001.1, . . . , 1001.N and tool datasets 1021.1, . . . , 1021.M, where a pick-up gesture dataset 1001.1, . . . , 1001.N can be assigned to a pick-up gesture, and a tool dataset 1021.1, . . . , 1021.M can be assigned to a first tool 601, 602, 603. In the example embodiment shown, N pick-up gesture datasets 1001.1, . . . , 1001.N have been registered and stored in a pick-up gesture list 1000. In the example embodiment shown, the M tool datasets 1021.1, . . . , 1021.M are stored in a tool list 1020, and the number M of tool datasets 1021.1, . . . , 1021.M (and hence also the length M of the tool list 1020) equals the number of tools 601, 602, 603 with which the user can interact.

In general, a pick-up gesture time 1002.1, . . . , 1002.N and a pick-up gesture position 1003.1, . . . , 1003.N can be assigned to a pick-up gesture. In the example embodiment shown, the pick-up gesture dataset 1001.1, . . . , 1001.N comprises the pick-up gesture time 1002.1, . . . , 1002.N and the pick-up gesture position 1003.1, . . . , 1003.N of the associated pick-up gesture.

In this case, the pick-up gesture time 1002.1, . . . , 1002.N can be based on the first time or the second time, in particular the pick-up gesture time 1002.1, . . . , 1002.N can lie between the first time and the second time, or in particular also be identical to the first time or the second time. In the example embodiment shown, the pick-up gesture time 1002.1, . . . , 1002.N is identical to the second time.

The pick-up gesture position 1003.1, . . . , 1003.N can be based on the first position 311.1 of the thumb 301 and/or on the first position 312.1 of the index finger 302. Alternatively, and as presented in the example embodiment shown, it is also possible that the pick-up gesture position 1003.1, . . . , 1003.N is based on the second position 311.2 of the thumb 301 and on the second position 312.2 of the index finger 302. In particular, the pick-up gesture position 1003.1, . . . , 1003.N can be arranged on the line between the first position 311.1 of the thumb 301 and the first position 312.2 of the index finger 302 or on the path between the second position 311.2 of the thumb 301 and the second position 312.2 of the index finger 302. In particular, it is also possible that the pick-up gesture position 1003.1, . . . , 1003.N is identical to the first position 311.1 or the second position 311.2 of the thumb 301 or to the first position 312.2 or the second position 312.2 of the index finger 302. Alternatively, it is also possible that the pick-up gesture position 1003.1, . . . , 1003.N is based both on the first position 311.1, 312.1 of the thumb 301 and of the index finger 302 and on the second position 311.2, 312.2 of the thumb 301 and of the index finger 302. In particular, the pick-up gesture position 1003.1, . . . , 1003.N can be defined as a weighted sum of spatial vectors of the positions on which they are based. In the example embodiment shown, the pick-up gesture position 1003.1, . . . , 1003.N is the center point between the second position 311.2 of the thumb 301 and the second position 312.2 of the index finger 302.

In the example embodiment shown, a pick-up gesture dataset 1001.1, . . . , 1001.N comprises a corresponding pick-up gesture time 1002.1, . . . , 1002.N and a corresponding pick-up gesture position 1003.1, . . . , 1003.N. The pick-up gesture time 1002.1, . . . , 1002.N in this example equals the second time of the associated pick-up gesture, the pick-up gesture position 1003.1, . . . , 1003.N equals the second position 311.2 of the thumb 301 of the associated pick-up gesture. It is alternatively also possible, however, to use another time as the pick-up gesture time 1002.1, . . . , 1002.N or another position as the pick-up gesture position 1003.1, . . . , 1003.N, in particular to use the first time as the pick-up gesture time 1002.1, . . . , 1002.N, or in particular to use the first position 311.1 of the thumb 301, the first position 312.1 of the index finger 302 or the second position 312.2 of the index finger 302 as the pick-up gesture position 1003.1, . . . , 1003.N.

In the example embodiment shown, the pick-up gesture datasets 1001.1, . . . , 1001.N are assigned to the tool datasets 1021.1, . . . , 1021.M by W assignment relations 1010.1, . . . , 1010.W. For example, the pick-up gesture dataset 1001.1 is assigned to the tool dataset 1021.2 via the assignment relation 1010.1, the pick-up gesture dataset 1001.2 is assigned to the tool dataset 1021.1 via the assignment relation 1010.2, and to the tool data set 1021.2 via the assignment relation 1010.3, and the pick-up gesture dataset 1001.N is assigned to the tool data set 1021.M via the assignment relation 1010.W.

It is possible that a pick-up gesture dataset 1001.1, . . . , 1001.N is not assigned to any tool dataset 1021.1, . . . , 1021.M (e.g. the pick-up gesture dataset 1001.3), in which case a first tool 601, 602, 603 is not assigned to the associated pick-up gesture. In addition, it is possible that a pick-up gesture dataset 1001.1, . . . , 1001.N is assigned to exactly one tool dataset 1021.1, . . . , 1021.M (e.g. pick-up gesture dataset 1001.1 or pick-up gesture dataset 1001.N), in which case there is a unique assignment between the associated pick-up gesture and the particular tool 601, 602, 603. In addition, a pick-up gesture dataset 1001.1, . . . , 1001.N can be assigned to a plurality of tool datasets 1021.1, . . . , 1021.M (e.g. pick-up gesture dataset 1001.2), in which case a plurality of tools 601, 602, 603 are assigned to the associated pick-up gesture. In certain embodiments, a pick-up gesture dataset 1001.1, . . . , 1001.N can be assigned to a maximum of one tool dataset 1021.1, . . . , 1021.M, in other example embodiments a pick-up gesture dataset 1001.1, . . . , 1001.N can be assigned to exactly one tool dataset 1021.1, . . . , 1021.M.

The assignment relations 1010.1, . . . , 1010.W in particular can be stored in the form of a sequence table. In particular, each element of this sequence table then comprises exactly one pick-up gesture dataset 1001.1, . . . , 1001.N and any number of tool datasets 1021.1, . . . , 1021.M, which are assigned to the pick-up gesture dataset 1001.1, . . . , 1001.N. In a preferred embodiment, the sequence table is ordered according to the pick-up gesture time 1002.1, . . . , 1002.N of the pick-up gesture datasets 1001.1, . . . , 1001.N.

TABLE A

| | |
|---|---|
| A.1 | pos__thb__1 = pos__detector.position__thumb( ) |
| A.2 | pos__ind__1 = pos__detector.position__index( ) |
| A.3 | wait(100ms) |
| A.4 | pos__thb__2 = pos__detector.position__thumb( ) |
| A.5 | pos__ind__2 = pos__detector.position__index( ) |
| A.6 | dist__1 = eucl__dist(pos__thb__1, pos__ind__1) |
| A.7 | dist__2 = eucl__dist(pos__thb__2, pos__ind__2) |
| A.8 | if dist__1 > 0.02 and dist__2 <= 0.02: |
| A.9 |     tool__nrst = tools[0] |
| A.10 |     dist__nrst = eucl__dist(pos__ind__2, tools[0]) |
| A.11 |     for tool in tools: |
| A.12 |         if eucl__dist(pos__ind__2, tool) < dist__nrst: |
| A.13 |             tool__nrst = tool |
| A.14 |             dist__nrst = eucl__dist(pos__ind__2, tool) |
| A.15 | gestures.store(now( ), tool, pos__ind__2) |

Table A shows pseudocode of an example embodiment of the method according to the invention. In code lines A.1 and A.2, functions "position_thumb" and "position_index" provided by the first position detector 240 "pos_detector" are used to determine the first position 311.1 of the thumb 301 and the first position 312.1 of the index finger 302 at the first time. Code line A.3 waits for a time interval of 100 ms in order for the second position 311.2 of the thumb 301 and the second position 312.2 of the index finger 302 to be determined at the second time in code lines A.4 and A.5. Therefore in this example embodiment, the time interval between the first time and the second time is 100 ms. In code lines A.6 and A.7, the Euclidean distance between the thumb 301 and the index finger 302 is determined at the first time and the second time respectively.

In code line A.8, it is determined whether the first distance is greater than the TI distance threshold value (2 cm in this embodiment), and whether the second distance is less than or equal to the TI distance threshold value. If this is the case, it is assumed that there is a pick-up gesture.

In code lines A.9 and A.10, it is first determined from the list of tool positions "tools" the tool position at the start of the list, and its distance from the second position 312.2 of the index finger 302. In code lines A.11 and A.12 it is determined for each tool position in the list whether its distance is less than the previously shortest distance of another tool position. If this is the case, this tool position is set as the new smallest tool position in A.13 and A.14. In this process, each tool position can always be related to the associated tool 601, 602, 603 and/or the associated tool dataset 1021.1, . . . , 1021.M.

In code line A.15, the identified pick-up gesture (characterized by the time stamp "now( )" of the current system time) can be saved together with the tool 601, 602, 603 or the tool dataset 1021.1, . . . , 1021.M that has the minimum distance and with the second position 312.2 of the index finger 302 in a table of the pick-up gestures.

TABLE B

| | |
|---|---|
| B.1 | pos_thb_1 = pos_detector.position_thumb( ) |
| B.2 | pos_ind_1 = pos_detector.position_index( ) |
| B.3 | wait(100ms) |
| B.4 | pos_thb_2 = pos_detector.position_thumb( ) |
| B.5 | pos_ind_2 = pos_detector.position_index( ) |
| B.6 | dist_1 = eucl_dist(pos_thb_1, pos_ind_1) |
| B.7 | dist_2 = eucl_dist(pos_thb_2, pos_ind_2) |
| B.8 | if dist_1 > 0.02 and dist_2 <= 0.02: |
| B.9 | tools_assigned = [ ] |
| B.10 | for tool in tools: |
| B.11 | if eucl_dist(pos_ind_2, tool) <= 0.03: |
| B.12 | tools_assigned.push_back(tool) |
| B.13 | gestures.store(now( ), tools, pos_ind_2) |

Table B shows pseudocode of another example embodiment of the method according to the invention. Code lines B.1 to B.9 correspond to code lines A.1 to A.9 of Table A.

Unlike the pseudocode in Table A, in code line A.9 an empty list "tools assigned" is initialized containing tools 601 or tool datasets 1021.1, . . . , 1021.M, which comprises one or more of the tools 601, 602, 603 assigned to the pick-up gesture. A tool 601, 602, 603 is assigned to this list in code lines B.11 and B.12 if its Euclidean distance from the second position 312.2 of the index finger 302 is less than or equal to 3 cm, and if its Euclidean distance from the second position 311.2 of the thumb 301 is less than or equal to 3 cm. This corresponds to the method shown in FIG. 9. In code line B.13, the list of the tools 601, 602, 603 or tool datasets 1021.1, . . . , 1021.M is assigned and saved in a similar way to code line A.15.

Figure 11:
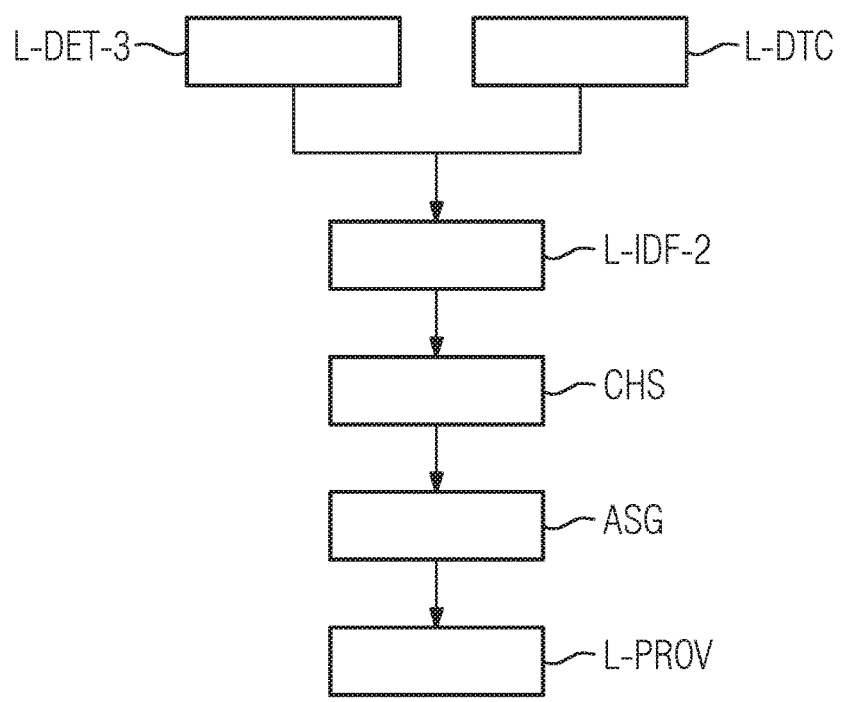
FIG. 11 is a flow diagram of a method for providing a sequence table for a user training session.

FIG. 11 shows an example embodiment of a method for providing a sequence table for a user training session. The first step of the example embodiment of the method shown in FIG. 11 is detecting L-DTC movements of the person 701 via a first position detector 240. In this example embodiment, the first position detector 240 comprises a motion capture system, which uses visual identification of position markers 321, 322 arranged on the person 701 to record the movements of the person 701. In particular, in this example embodiment the movements of the thumb 301 of a hand 300 and of the index finger 302 of the hand 300 are detected. This can be done in each case in particular by arranging a first position marker 321 on the thumb 301 of the hand 300, and a second position marker 322 on the index finger 302 of the hand 300.

The second step of the example embodiment of the method shown in FIG. 11 is the third determination L-DET-3, which determines via a second position detector 260 a set of tools with which a person 701 can interact during the user training session. In the example embodiment shown, the second position detector 260 comprises an RFID reader, and in addition a tool position marker 611, 612, 613 in the form of an RFID transponder is arranged on each of the tools 601, 602, 603. In this case, the RFID reader can establish the ID of RFID transponders that are at a distance from the RFID reader that is less than a threshold value. The particular tool 601, 602, 603 can then be identified from the ID of the RFID transponders. In addition, this arrangement can also be used to determine the position of the RFID transponders and hence the tools 601, 602, 603.

The detection step L-DTC and the third determination step L-DET-3 are independent of each other in this case and can be performed in any order; in particular the detection step L-DTC and the third determination step L-DET-3 can also be performed in parallel.

The third step of the example embodiment of the method shown in FIG. 11 is the second identification L-IDF-2, which identifies via a processing unit 222 a pick-up gesture based upon a movement of a thumb 301 of a hand 300 of the person 701 and of an index finger 302 of the hand 300 of the person 701. In the example embodiment shown, the second identification L-IDF-2 is formed by the substeps of the first determination DET-1, the first calculation CALC-1, the second determination DET-2, the second calculation CALC-2 and the first identification IDF-1 belonging to the example embodiment of a method shown in FIG. 1 for assigning a pick-up gesture to a first tool 601, 602, 603.

The fourth step of the example embodiment of the method shown in FIG. 11 is selecting CHS a first tool 601, 602, 603 from the set of tools via the processing unit 222 based upon a tool position of the first tool 601, 602, 603; the fifth step of the example embodiment of the method shown in FIG. 11 is assigning ASG the first tool 601, 602, 603 to the pick-up gesture via the processing unit 222. These two steps correspond to the steps of the example embodiment of the method shown in FIG. 1 for assigning a pick-up gesture to a first tool 601, 602, 603.

The sixth step of the example embodiment of the method shown in FIG. 11 is providing PROV via an interface 221 a sequence table comprising at least the time 1002.1, . . . , 1002.N of the pick-up gesture and the assigned tool 601, 602, 603. In the example embodiment shown, the sequence table is provided in the form of the assignment table shown in FIG. 10, in which a tool 601, 602, 603 can be identified by a tool dataset 1021.1, . . . , 1021.M.

The example embodiment of the method shown in FIG. 11 for providing a sequence table for a user training session can be performed in the assignment system 200 shown in FIG. 2 if the assignment system 200 shown in FIG. 2 is designed to perform the corresponding steps of the method for providing a sequence table for a user training session. Such an assignment unit can then be identified by a provision unit.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for assigning a first tool to a pick-up gesture, comprising:
    determining via a first position detector, as a first determination, a first position of a thumb of a hand of a person at a first time and a first position of an index finger of the hand at the first time;
    calculating via processing circuitry, as a first calculation, a first distance between the thumb and the index finger at the first time, the first distance based upon the first position of the thumb and the first position of the index finger;
    determining via the first position detector, as a second determination, a second position of the thumb at a second time and a second position of the index finger at the second time, the second time being later in time than the first time;
    calculating via the processing circuitry, as a second calculation, a second distance between the thumb and the index finger at the second time, the second distance based upon the second position of the thumb and the second position of the index finger;
    identifying via the processing circuitry, the pick-up gesture based upon the first distance and the second distance;
    selecting via the processing circuitry, the first tool from a set of tools based upon a tool position of the first tool, the first tool being a real tool;
    assigning via the processing circuitry, the first tool to the pick-up gesture; and
    providing via an interface, a sequence table including at least one data set representing the first tool and at least one time of the pick-up gesture.

2. The method of claim 1, wherein the identifying the pick-up gesture includes identifying the pick-up gesture based upon the first distance being greater than a threshold distance value and upon the second distance being less than or equal to the threshold distance value.

3. The method of claim 2, wherein the selecting the first tool is further based on either:
    at least one of the first position of the thumb or the first position of the index finger; or
    at least one of the second position of the thumb or the second position of the index finger.

4. The method of claim 3, wherein the selecting the first tool includes selecting the first tool such that the distance of the tool position from at least one of the second position of the thumb or the second position of the index finger is less than the threshold distance value.

5. The method of claim 4, wherein the selecting the first tool includes selecting exactly one first tool, and wherein the distance of the exactly one first tool from the second position of the thumb or from the second position of the index finger is less than or equal to a distance of each tool of the set of tools from the second position of the thumb or from the second position of the index finger.

6. The method of claim 3, wherein the selecting the first tool includes selecting exactly one first tool, and wherein the distance of the exactly one first tool from the second position of the thumb or from the second position of the index finger is less than or equal to a distance of each tool of the set of tools from the second position of the thumb or from the second position of the index finger.

7. The method of claim 2, further comprising:
    determining, via a second position detector, the tool position based upon a tool position marker arranged on the first tool.

8. The method of claim 2, further comprising:
    determining, via a visual imaging system, the tool position based on at least one visual image from the visual imaging system.

9. The method of claim 2,
    wherein a first position marker is on the thumb,
    wherein a second position marker is on the index finger,
    wherein the determining the first position of the thumb and the determining the second position of the thumb include locating the first position marker, and
    wherein the determining the first position of the index finger and the determining the second position of the index finger include locating the second position marker.

10. The method of claim 9, wherein the first position detector comprises a visual imaging system, and wherein the first position marker and the second position marker are located in a visual image.

11. A non-transitory computer program product including a computer program, directly loadable into a memory of an assignment system, the computer program including program segments to perform the method of claim 2 when the program segments are executed by the assignment system.

12. A non-transitory computer-readable medium, storing program segments readable and executable by an assignment system to perform the method of claim 2 when the program segments are executed by the assignment system.

13. The method of claim 1, wherein the selecting is also based on either
    at least one of the first position of the thumb or the first position of the index finger; or
    at least one of the second position of the thumb or the second position of the index finger.

14. The method of claim 13, wherein the selecting the first tool includes selecting the first tool such that the distance of the tool position, from at least one of the second position of the thumb and the second position of the index finger, is less than a threshold distance value.

15. The method of claim 14, wherein the selecting the first tool includes selecting exactly one first tool, and wherein the distance of the exactly one first tool from the second position of the thumb or from the second position of the index finger is less than or equal to a distance of each tool of the set of tools from the second position of the thumb or from the second position of the index finger.

16. The method of claim 13, wherein the selecting the first tool includes selecting exactly one first tool, and wherein the distance of the exactly one first tool from the second position of the thumb or from the second position of the index finger is less than or equal to a distance of each tool of the set of tools from the second position of the thumb or from the second position of the index finger.

17. The method of claim 1, further comprising:
determining, via a second position detector, the tool position based upon a tool position marker arranged on the first tool.

18. The method of claim 1, further comprising:
determining, via a visual imaging system, the tool position based on at least one visual image from the visual imaging system.

19. The method of claim 1, wherein the selecting the first tool includes selecting the first tool from a subset of the set of tools, each tool of the subset of the set of tools being at a distance from the person that is less than a threshold distance value.

20. The method of claim 1, wherein the first position detector includes a visual imaging system, wherein for the first determination, a first visual image is acquired, and at least one of the first position of the thumb or the first position of the index finger is determined based upon the first visual image, and wherein for the second determination, a second visual image is acquired, and at least one of the second position of the thumb or the second position of the index finger is determined based upon the second visual image.

21. The method of claim 1,
wherein a first position marker is on the thumb,
wherein a second position marker is on the index finger,
wherein the determining the first position of the thumb and the determining the second position of the thumb include locating the first position marker, and
wherein the determining the first position of the index finger and the determining the second position of the index finger include locating the second position marker.

22. The method of claim 21, wherein the first position detector comprises a visual imaging system, and wherein the first position marker and the second position marker are located in a visual image.

23. A non-transitory computer program product including a computer program, directly loadable into a memory of an assignment system, the computer program including program segments to perform the method of claim 1 when the program segments are executed by the assignment system.

24. A non-transitory computer-readable medium, storing program segments readable and executable by an assignment system to perform the method of claim 1 when the program segments are executed by the assignment system.

25. The method of claim 1, wherein the selecting the first tool from the set of tools includes selecting a plurality of tools from the set of tools.

26. The method of claim 1, wherein the selecting the first tool from the set of tools includes selecting the first tool based on the first tool being located within a tool position region, the tool position region being one of:

a cylinder having a main axis corresponding to a line between the second position of the thumb and the second position of the index finger, or
a volume of intersection of a first sphere and a second sphere, the first sphere having a first center at the second position of the thumb, the second sphere having a second center at the second position of the index finger, and the first and second spheres having first and second radii equal to a threshold distance value.

27. An assignment system for assigning a first tool to a pick-up gesture, the assignment system comprising:
a first position detector configured to,
determine a first position of a thumb of a hand of a person and a first position of an index finger of the hand at a first time, and
determine a second position of the thumb and a second position of the index finger at a second time, the second time being later in time than the first time; and
processing circuitry configured assignment system to,
calculate a first distance between the thumb and the index finger at the first time, the first distance based upon the first position of the thumb and the first position of the index finger,
calculate a second distance between the thumb and the index finger at the second time, the second distance based upon the second position of the thumb and the second position of the index finger,
identify the pick-up gesture based upon the first distance and the second distance,
select the first tool from a set of tools, the selection based upon a tool position of the first tool, the first tool being a real tool,
assign the first tool to the pick-up gesture, and
provide, via an interface, a sequence table including at least one data set representing the first tool and at least one time of the pick-up gesture.

28. The assignment system of claim 27, wherein the processing circuitry is further configured to cause the assignment system to
identify the pick-up gesture based upon the first distance being greater than a threshold distance value and upon the second distance being less than or equal to the threshold distance value.

29. A method for providing a sequence table for a user training session, the method comprising:
detecting movements of a person;
determining a set of tools usable by the person during the user training session;
identifying a pick-up gesture based upon movement of a thumb of a hand of the person and of an index finger of the hand of the person;
selecting a first tool from the set of tools based upon a tool position of the first tool;
assigning the first tool to the pick-up gesture; and
providing the sequence table via an interface, the sequence table including at least one data set representing the first tool and at least one time of the pick-up gesture.

* * * * *